United States Patent [19]

Kramer et al.

[11] Patent Number: 5,320,805
[45] Date of Patent: Jun. 14, 1994

[54] METHODS OF USING A CLEANER, SANITIZER, DISINFECTANT, FUNGICIDE, SPORICIDE, CHEMICAL STERILIZER

[75] Inventors: David N. Kramer, Stevenson, Md.; Shira Kramer, Ardmore, Pa.

[73] Assignee: Sterilex Corporation, Haverford, Pa.

[21] Appl. No.: 699,611

[22] Filed: May 15, 1991

[51] Int. Cl.$^5$ .................. C11D 3/48; A01N 25/00; A01N 39/00

[52] U.S. Cl. .................................. 422/28; 422/37; 252/106; 424/616; 424/405

[58] Field of Search .............. 422/20, 21, 24, 28, 422/37; 426/521; 252/95, 102, 106; 134/2, 22.1, 22.13, 42; 424/616, 405, 411

[56] References Cited

U.S. PATENT DOCUMENTS

| | | | |
|---|---|---|---|
| 3,640,874 | 2/1972 | Gray | 252/95 |
| 3,753,651 | 8/1973 | Baucher | 422/21 |
| 3,925,241 | 12/1975 | Schmolka | 252/316 |
| 4,120,809 | 10/1978 | Murray | 252/102 |
| 4,448,750 | 5/1984 | Fuesting | 422/20 |
| 4,847,089 | 7/1989 | Kramer et al. | 424/405 |
| 4,850,729 | 7/1989 | Kramer et al. | 401/183 |
| 4,896,042 | 1/1990 | Humphreys | 250/435 |
| 4,941,989 | 7/1990 | Kramer et al. | 252/102 |

OTHER PUBLICATIONS

Block, *Disinfection, Sterilization, & Preservation*, 1983, pp. 321-325.

*Primary Examiner*—Robert J. Warden
*Assistant Examiner*—T. A. Trembley
*Attorney, Agent, or Firm*—Cushman, Darby & Cushman

[57] ABSTRACT

A method of using a chemical composition as a cleanser, sanitizer, disinfectant, sporicide, fungicide and sterilizer by applying an effective amount of the composition to objects and surfaces requiring the application of a cleanser, sanitizer, disinfectant, sporicide, fungicide or sterilizer, the composition including from about 10% to about 90% by weight of an alkaline water-soluble salt having hydrogen peroxide of crystallization and from about a fraction of a percent to about 30% by weight of a positively charged phase-transfer agent selected from the group consisting of a phosphonium salt, a sulfonium salt, and a quaternary ammonium salt, said composition forming both a water and lipid soluble phase-transfer ion-pair.

8 Claims, No Drawings

METHODS OF USING A CLEANER, SANITIZER, DISINFECTANT, FUNGICIDE, SPORICIDE, CHEMICAL STERILIZER

FIELD OF THE INVENTION

This invention relates to methods of using compositions which find utility as cleaners/sanitizers/disinfectants/fungicides/sporicides and sterilizers. Such methods are applicable, for example, in health care, medical (e.g. surgical) applications and food processing operations.

BACKGROUND OF THE INVENTION

Most conventional sterilizers are ineffective, dangerous to handle and/or difficult to use.

At present, the available chemical sterilizers include ethylene oxide, formaldehyde, glutaraldehyde and peracids.

Ethylene oxide sterilizer is a toxic gas and requires that protective equipment and devices be used. Formaldehyde and glutaraldehyde are toxic liquids and require extreme care, prolonged exposure, (3 hours or longer) and before use, surfaces must be meticulously cleaned. Additionally, the liquid sterilizers suffer from one or more deficiencies, such as skin irritation, offensive or irritating odor and inhalation toxicity; deleterious effect on fabrics and painted surfaces and waste disposal systems (or environmental toxicity); lack of stability; and low level of efficacy. Peracids are highly toxic, corrosive and unstable.

The methods of the present invention are highly effective and include using a composition that is capable of inactivating (killing) micro-organisms including bacterial and fungal spores at room temperature such that the initial count is reduced to zero in EPA-specified tests (AOAC Manual for Sporicidal Testing, Chapter 14) involving *Bacillus subtilis* and *Clostridium sporogenes, Pseudomonas aeruginosa* and *Staphyloccus aureus.*

In use, the composition of the present invention is employed as a cleaner, sanitizer, disinfectant, and chemical sterilizer. The numerous advantages of this invention with respect to its methods of use and applications are summarized below.

SUMMARY OF THE INVENTION

The methods of using the invention exhibit a number of improvements over methods employing prior art compositions. The present methods of cleaning, sanitizing, disinfecting, and sterilizing (including killing spores) are effective, non-toxic, environmentally safe and readily available. The methods of using the compositions of the present invention do not cause an offensive or irritating odor. The compositions are, in fact, non-volatile. Moreover, the compositions are not corrosive towards metals, plastics, and fabrics. In addition, the compositions exhibit a high level of efficacy as rapid, ambient temperature disinfectant chemical sterilizers and have excellent stability characteristics.

It is therefore an object of this invention to provide new and unique systems and methods for using the compositions.

It is still another object of this invention to provide systems and methods of using the compositions that are not toxic to humans and other mammals, not irritating to human skin and that do not cause offensive or irritating odors.

Another object of this invention is to provide systems and methods of using a chemical sterilizer that are not corrosive towards metals, plastics and fabrics.

Still another object of this invention is to provide highly efficacious and rapid systems and methods of using a chemical sanitizer/disinfectant/sporicide/sterilizer.

The foregoing and other objects as defined herein are accomplished by the practice of this invention. Broadly viewed in one of its principal aspects, this invention consists of methods of using cleansing, sanitizing, disinfecting, sporioidal and chemical sterilizing compositions at an effective concentration. The compositions include an alkaline water-soluble salt having hydrogen peroxide of crystallization and a positively charged phase-transfer agent.

In addition to utility as cleaners, sanitizers, and disinfectants, and sporicides, the instant invention thus provides systems and methods of use that finds utility in health care, as sterilizing procedures in surgical applications and more broadly, as chemical sterilizers applicable to the sterilization of medical, dental and veterinary equipment and objects, skin and wound lavage, health spas, operating rooms, surgical hand scrubs, animal grow-out rooms, cow teats, baby nurseries and wherever disinfection and sterilization of various objects both animate and inanimate are required. The composition employed in the methods of this invention do not produce toxic fumes, are not irritating to the skin, have no offensive or irritating odor, are not corrosive, have excellent stability, are biodegradable and are rapid and highly effective cleansing, disinfecting and sterilizing agents.

The composition of this invention finds uses in food processing plants for human and animal consumption and may include: meat, fish, poultry, turkey, dairy, beverage, baking, salads, sausage, canning, and pet food industries. Other uses include plants manufacturing animal litter, pickling products, fruit juices, and vegetable products.

Further methods of employing the present composition are in the pharmaceutical field such as in cleansing, disinfecting and sterilizing pharmaceutical manufacturing equipment, production lines or portions thereof.

An additional object of this invention is to afford food processing plants a means for cleaning/sanitizing/disinfecting/sterilizing methods and materials which have high detergency, water and oil solubility, foaming, hydrolytic and efficacy, high antimicrobial activity and at the same time may be dispensed as a powder (e.g.—on floors, drains), foam, high pressure spray, hand scrub, boot dip, gel, as well as in tablet and packet form.

Other methods of using the composition are employed at the origin of the food production chain as in grow-out structures, egg washing, pens and crates where cleaning and sanitation and disinfection are necessary to prevent food contamination.

Another embodiment of the invention is the methods and materials of utility as a cleaning/sanitizer/disinfectant/mildicide and sterilizer for use in the household. In the realm of the consumer, such uses include, but are not limited to, applications to toilets, showers, kitchens, baby nurseries, personal hygiene, contact lenses, refrigerators, floors, walls, ceilings, hot houses (for plants), vehicles, clothing, laundering, toys, utensils and dishes.

A further method of use of the composition of the invention is in marine applications as a cleaning/sanitizing/disinfecting/fungicide and sterilizing means for boats, yachts, and liners; wherein the composition is used to remove microbial, fungal, and algal contamination, discolorations and slimes from, upon and within the vessel.

Still a further instance of use and applications is as a method and material in the cleaning/sanitizing disinfection and sterilizing of medical wastes and of protective clothing designed for handling toxic and medical wastes, in sterile environments of manufacturing plants, in space suits and vehicles, and in aircraft and other modes of transportation requiring disinfection or sterilization.

The nature and substance of the present invention as well as its objects and advantages will be more clearly perceived and fully understood by referring to the following description and claims taken in connection with the accompanying drawings which are described briefly below.

DESCRIPTION OF THE PREFERRED EMBODIMENTS

The systems and methods of using chemical sterilizers, disinfectants, and sanitizers of this invention are thus characterized by having broad utility, for example, in human and animal health care, as sterilizing methods in surgical applications and in food processing plants. The compositions employed in this invention comprise an alkaline water-soluble salt having hydrogen peroxide of crystallization and a positively charged phase-transfer agent. Depending on the intended use, the compositions of this invention may also contain various additives. For example, the compositions may advantageously contain a surfactant. The compositions may also contain peroxide activators such as enzymes, iodides, and hemin; perfumes such as rose oil; dyes such as fluorescein; emollients such as lanolin and glycol derivatives; gelling agents such as carboxymethyl cellulose; clays such as kaolinite, attapulgite and bentonite; metal peroxides such as calcium peroxide and peracids such as perboric, persulfuric, perphosphoric and peracetic acids. Examples of suitable enzymes are horseradish peroxidase, lactoperoxidase and myeloperoxidase. Moreover, builders may be incorporated such as sodium phosphates, sodium silicates and ethylene diamine tetra acetate for the purpose of removing water hardness.

In one embodiment, the present invention includes methods of using a chemical composition as a cleanser, sanitizer, disinfectant, sporicide, fungicide and sterilizer by applying an effective amount of the composition to objects and surfaces requiring the application of a cleanser, sanitizer, disinfectant, sporicide, fungicide or sterilizer, the composition comprising from about 10% to about 90% by weight of an alkaline water-soluble salt having hydrogen peroxide of crystallization and from about a fraction of a percent to about 30% by weight of a positively charged phase-transfer agent selected from the group consisting of a phosphonium salt, a sulfonium salt, and a quaternary ammonium salt, the composition forming both a water and lipid soluble phase-transfer ion-pair within a medium having pH greater than 9.5.

The compositions of this invention may be compounded in various forms suitable for particular end methods of use. Thus, compositions may be formulated as creams, bulk powders, tablets, soaps, foams, gels, aerosols and solutions. In addition, they may be incorporated into towels, wipes, sponges and brushes.

The peroxide salts used in the practice of this invention are alkaline water-soluble salts having hydrogen peroxide of crystallization or forms peroxide upon dissociation (e.g. sodium carbonate-hydrogen peroxide of crystallization). When the salts are dissolved in water, peroxide ion is released. Other examples of suitable per-salts are perborates, persilicates, persulfates, peracetates and perphosphates associated with a cation that will give an alkaline water-soluble peroxy salt. Examples of suitable cations are the alkali metals; especially preferred is "sodium percarbonate" having the empirical formula $2(Na_2CO_3)$—$nH_2O_2$, where n=1, 2 or 3, "sodium percarbonate" having the hydrogen peroxide of crystallization.

It should be noted that per-salts and perhydroxyl ions alone are mild disinfectants but are superior when used in the presence of a cationic phase transfer agent.

The positively charged phase-transfer agent may be a phosphonium salt such as t-butyl phosphonium iodide, a sulfonium salt such as tributyl sulfonium chloride, or a quaternary ammonium salt. The choice of the positively charged ion in the phase-transfer agent is critical. The choice of the counter anion in the phase-transfer agent is not critical in this regard. The hydrocarbyl groups attached to the phosphorous, sulfur or nitrogen must contain a total number of carbons such that the compound is water-soluble but yet has sufficient lipophilic character to permit it to pass from the aqueous phase into a non-polar oil (or organic) phase. Also, the ion-pair formed between the positively charged ion and negatively charged ion must be an intimate ion-pair that is not dissociated in the solution. The phase-transfer agents become disinfecting and sterilizing as they become lipophilic and thus are able to penetrate and destroy biofilms and microbial cells.

The preferred positively charged phase-transfer agents are quaternary ammonium salts having a chain of carbon atoms of ca. 4 to 30, preferably ca. 6 to 30, and most preferably ca. 8 to 25, in length on the quaternary nitrogen. The number of carbons on the nitrogen of the quaternary ammonium salt, as mentioned, is critical. The quaternary ammonium salt must not only be water-soluble but it must also possess sufficient lipophilic character to permit it to pass from the aqueous phase into an oil (or organic) phase when forming an ion-pair with peroxide ion. As mentioned above, when the alkaline salt containing hydrogen peroxide of crystallization is dissolved in an aqueous solution of a positively charged ion such as a quaternary ammonium salt, the alkaline salt extracts a proton from the hydrogen peroxide, leaving the negatively charged hydroperoxide ion. The hydroperoxide ion then becomes intimately associated with the quaternary ammonium ion and its negative charge is effectively neutralized:

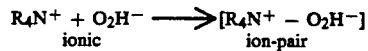

The resultant lipophilic quaternary ammonium hydroperoxide ion pair may then pass from the aqueous phase into an oil, or organic phase where the hydroperoxide ion may exert its decontamination disinfecting and sterilizing effects. While quaternary ammonium salts are decontaminants and disinfectants themselves but not sterilizers, these properties are enhanced synergistically to form sterilizers when they are combined with a per-salt.

U.S. Pat. No 2,917,428 discloses an aqueous disinfecting solution composition containing a quaternary ammonium halide, hydrogen peroxide and acetate salts of saturated acyclic amines, which are slightly acidic. Since the aqueous medium must be alkaline, e.g., having a pH equal to or greater than ca. 9.5, and preferably greater than 10.5 before a proton can be extracted from hydrogen peroxide to a significant extent, i.e., approximately half ionized, the compositions in U.S. Pat. No. 2,917,428 cannot form the quaternary ammonium hydroperoxide phase-transfer complex which is critical to the instant invention.

In one embodiment of the present invention, the present composition is used in solution form having a pH of at least 10.5.

In the practice of this invention, a single positively charged phase-transfer agent or a mixture of positively charged phase-transfer agents may be used. Particularly suitable positively charged phase-transfer agents are didecyl dimethyl ammonium chloride (DDDM), and/or tetradecyl dimethyl benzyl ammonium chloride.

It is noted that an essential element in the invention is to render the phase-transfer ion-pair soluble in water and in lipids, rendering the ion-pair properties which do not exist in the individual components.

While the cleansing, disinfecting and sterilizing compositions of this invention do not require a surfactant, preferred compositions contain one or more surfactants. The surfactant disperses the contamination to be cleansed, disinfected or sterilized, thus increasing its surface area and enhancing its contact by the quaternary ammonium hydroperoxide as well as favoring its transfer into a non-polar phase.

The surfactant used in the compositions of this invention may be a nonionic surfactant, an anionic surfactant, a cationic surfactant, or mixtures thereof. Examples of suitable nonionic surfactants are linear alkoxylates; e.g. polyoxypropylene and polyoxyethylene block copolymer (i.e. Pluronic).

The cleansing, disinfecting and sterilizing compositions of this invention broadly contain ca. 10% to 90% by weight of alkaline water-soluble salt containing hydrogen peroxide of crystallization, and preferable ca. 20% to 77% by weight of alkaline water-soluble salt containing hydrogen peroxide of crystallization. The compositions of the invention contain a positively charged phase-transfer agent in the broad range of from a fraction of a percent to ca. 30% by weight, and preferable in the range of ca. 1% to 23% by weight. The amount of surfactant in the composition of the invention, if a surfactant is present, is broadly within the range of ca. 0.25% to 20% by weight, and preferably within the range of ca. 1% to 15.1% by weight.

The surfactant may be, for example, a linear alkoxylate, an alkylphenol ethoxylate, and mixtures thereof.

In addition to the foregoing, the compositions of the invention may contain other additives such as perfumes, dyes, enzymes, metal peroxides, builders and emollients.

Thus, the instant invention provides improved cleansing, disinfecting and sterilizing compositions that are characterized by a number of advantages over cleansing, disinfecting and sterilizing compositions of the prior art. The methods of using such a chemical sterilizing composition are accordingly improved.

With respect to sterilization, in one embodiment, the present invention includes methods of using a chemical sterilizer to sterilize objects and surfaces in medical, dental and veterinary applications requiring sterilization by applying a sterilizing effective amount of the sterilizer, the sterilizer including a composition comprising from about 10% to about 90% by weight of an alkaline water-soluble salt having hydrogen peroxide of crystallization, from about a fraction of a percent to about 50% by weight of a positively charged phase-transfer agent the composition forming both a water and lipid soluble ion pair.

As a chemical sterilizer, the composition of one embodiment of the present invention is applied at a concentration of 0.1% to 20% (W/V) for exposure times of 1 minute to 4 hours at ambient temperatures. In another embodiment, the composition is applied at a concentration of 1% (W/V) for an exposure time of about 15 minutes at 50° C. or greater.

The sterilizing effect of the present composition may be enhanced by simultaneous application of ultrasonic, microwave and/or ultraviolet radiation.

The exposure of the chemical reactants in aqueous media to microwave results in enhanced reactivity due to acceleration of rates of reaction. The increase in reaction rate is due to increase in temperature. With respect to the sporicidal activity of the present composition, raising the temperature from 20° C. to 50° C. results in complete spore skill whereas at the lower temperature (20° C.) the spores are unaffected.

Ultra-violet radiation has germicidal activity and there are commercial systems serving the purpose of destroying organisms by exposure to ultra-violet radiation in the 200 to 380 millimicron range. The mechanism attributed to the antimicrobial effects are the formation of free hydroxyl radical within the water vapor in the atmosphere which radicals lethally react by a zero order kinetics with the microorganisms. With respect to the present invention, ultra-violet irradiation in combination with the peroxide in solutions of the present composition dissociates the peroxide ions into perhydroxyl and hydroxyl free radicals which lethally react rapidly with the microorganisms.

Not only are the compositions of this invention comprised of readily available and relatively inexpensive components, but the compositions in use concentrations are not irritating to the skin. They do not have an offensive odor and are non-volatile. In addition, the compositions are noncorrosive and are, in many instances, anti-corrosive. They also exhibit a high level of efficacy as rapid cleansing, disinfecting and sterilizing agents. Moreover, the compositions have excellent stability.

The food industry is waging a constant battle with microbial contamination. Mechanical equipment and a variety of chemicals are being used for cleaning and sanitizing.

Yet, microbial contamination in food plants and food products persist. Of greatest concern today are *Listeria monocytogenes*, *Salmonella cholerasuis* and bacterial spores.

Generally used cleaning/sanitizing/disinfecting methods employ steam and chemicals such as caustic chlorine bleach, iodine, and quaternary ammonium compounds. However, these chemicals are effective only if the surface is first thoroughly cleaned. There is evidence that these water-based chemicals do not remove biofilms and are also hazardous to personnel and corrosive to equipment.

In one embodiment of the present invention, when an object or surface is contaminated with microorganisms including fungal spores, the effective amount of the composition is a 0.1–1.0% concentration by weight, the composition consisting of 70% (wt) of an alkaline water-soluble salt having hydrogen peroxide of crystallization with sodium carbonate, 20% (wt) of tetradecyl-dimethyl-benzyl-ammonium chloride and 10% (wt) of ethoxy-propoxy block polymer. When the object or surface is contaminated with fungal spores at least one effective amount of the composition is a 1.0% concentration applied for 15 to 25 minutes at about 20° C. When the object or surface is contaminated with bacterial spores at $10^6$/ml to $10^7$/ml level at least one effective amount of the composition is applied for up to 2 hours at ambient temperature, to result in 100% kill.

In demonstrating the high efficacy of the present composition in sterilizing activity, spores were chosen to use in the sterilizing protocol and methods of testing were chose to represent extreme conditions to encompass efficacy to all microorganisms including viruses, flukes, spirocetes, bacteriophages and other such pathogenic microbials (Dr. Karl Olsen, National Food Processors Lab, Dublin, Calif. and Dr. Robert Nauman, Department of Microbiology, University of Maryland, School of Dentistry, Baltimore, Md.

Biofilms are residues on surfaces that had been previously cleaned with caustic, steam, bleach and quaternary ammonium compounds. These films are accumulations of lipids, proteins, grime and micro-organisms that are air and light oxidized and polymerized and behave like tenacious glues.

Since biofilms are lipids, water-based products do not penetrate them nor remove them, with the result that they behave as focal points of bacterial contamination, especially with respect to Listeria monocytogenes and Salmonella enteridites.

The present invention is unique in this regard in that not only are its solutions water soluble, they are soluble by virtue of the phase transfer ion-pair in lipids. The phase transfer ion-pair is thus capable of penetrating biofilms, and homogeneously mixing the peroxide ion with the lipids and proteins, thus facilitating rapid saponification and destruction of the film. Moreover, the microbial membranes are also surrounded by a biofilm composed of lipopolysaccharide and glycoprotein which are penetrated by the phase transfer ion-pair and are similarly destroyed. Also, having penetrated the microbial cell, the composition inhibits intracellular enzymes such as esterases, peptidases, kinases and catalases leading to microbial lethality. The reaction with spores proceeds by the same mechanisms, which explains why the compositions of the invention are sporicides/sterilizers at relatively low concentrations, in the 2,000-4,000 ppm range, while the quaternary ammonium salts (quats) and the peroxide salts alone are effective only as sanitizers and disinfectants even at very high concentrations.

Further, bleach and quats become ineffective since they are inactivated and rendered ineffective in the presence of organic material such as fat, protein, blood and dirt. In addition to being ineffective cleaners, they do not reach the contaminating bacteria unless there is thorough cleaning beforehand.

Even where cleaning efforts are inconsistent and inadequate, the composition of this invention is also a cleaner and is effective in the removal of biofilms and in sanitizing, disinfecting and sterilizing applications. The composition has been shown to remove Listeria and Salmonella contamination even where there is inadequate cleaning. Moreover, contaminated equipment may be cleaned by soaking in solutions of the composition for effective decontamination.

The present methods of using the composition may employ the composition in the form of a gel, cream, tablets or bulk powder.

In one embodiment the composition is made up as a gel by adding to a 4-6% aqueous solution of the composition (e.g. the 70:20:10 composition set forth in following Example 1), carboxymethyl cellulose in an amount up to 9-11%.

A cream may be made by slurrying 18-22% of the composition (e.g. the 70:20:10 composition of Example 1) to a cream base consisting of 27-33% ethylene glycol and 63-77% polyethoxy polypropoxy block polymer.

The bulk powder of the composition may be manufactured by blending the required proportions of the ingredients of particular embodiments employing a screw type grinder blender for about one hour preferably under anhydrous conditions.

The bulk powder may be tabletted by adding an additional 9-11% of polyethoxy polypropoxy bulk polymer and pressed in a tabletting press at about 2000 psi.

The advantages of methods of using the present composition are that the composition is: effective, kills spores, viruses, bacteria and fungi; non-solvent; non-volatile; water soluble and fat-soluble; biodegradable; non-corrosive/anticorrosive; amenable for use in high pressure washers, foamers and scrubbers and a wide variety of delivery systems; a mildew inhibitor; a means of destroying odors; a versatile and universal cleaner; safe; and cost effective.

The invention will be more clearly perceived and better understood from the following specific examples.

EXAMPLES

Example 1

A representative test sample of the present composition was prepared: Composition A. The constituents of Composition A are as follows:

| A. The constituents of Composition A are as follows: COMPOSITION A (70:20:10) | |
|---|---|
| Sodium Carbonate-Hydrogen Peroxide "Sodium Percarbonate" | 70% |
| Tetradecyl-dimethyl-benzyl-ammonium chloride | 20% |
| Polyethoxy polypropoxy block polymer | 10% |

To determine the sporicidal and sterilant activities of Composition A, tests were carried out with a 15% weight per volume (W/V) solution in sterile deionized water. The test was a time-kill determination at ambient temperature (26° C.). The pH of the solution at the beginning and conclusion of the test was 10.75. The results, including sampling times and log reductions are given below. Also, the D-value is presented.

To test for neutralization of the mixture, spores of Bacillus subtilis were added to the neutralized solution after standing for 5 minutes:

| Added spore recovered spores | 75 |
|---|---|
| Sample 1 | 66 |
| Sample 2 | 65 |

In the test, $9.8 \times 10^6$ spores were added in suspension and serial samples were taken and plated.

| TIME | RECOVERY |
| --- | --- |
| 0 min. | $9.8 \times 10^6$/ml |
| 10 min. | — |
| 20 min. | $3.5 \times 10^6$ |
| 30 min. | — |
| 40 min. | $7.3 \times 10^5$ |
| 60 min. | $1.8 \times 10^4$ |
| 80 min. | $2.9 \times 10^1$ |
| 90 min. | — |
| 100 min. | 3/ml |
| 120 min. | 0 |
| 150 min. | 0 |
| 180 min. | 0 |
| 210 min. | 0 |
| 240 min. | 0 |
| 270 min. | 0 |
| 300 min. | 0 |
| 330 min. | 0 |
| 360 min. | 0 |

One log, D value, reduction required 15.2 minutes

EXAMPLE 2

To determine the sporicidal and sterilant activities of the 70:20:10 composition (Composition A, from Example 1), tests were carried out with a 7.5% W/V solution in sterile deionized water. The test was a time-kill determination at ambient temperature (26° C.).

The pH of the solution at the beginning and conclusion of the test was 10.75. The results, including sampling times and log reductions are given below. Also, the D-value is presented. To test for neutralization of the mixture, spores of Bacillus subtilis were added to the neutralized solution after standing for 5 minutes:

| Added spore recovered spores | 75 |
| --- | --- |
| Sample 1 | 66 |
| Sample 2 | 65 |

In the test, $1.32 \times 10^7$ spores were added in Suspension and serial samples were taken and plated.

| TIME | RECOVERY |
| --- | --- |
| 60 min. (1 hr) | $4.5 \times 10^6$ |
| 90 min. (1 hr 30 min) | $3.85 \times 10^6$ |
| 120 min. (2 hr) | $1.7 \times 10^6$ |
| 150 min. (2 hr 30 min) | $3.45 \times 10^5$ |
| 180 min. (3 hr) | $6.23 \times 10^4$ |
| 110 min. (3 hr 30 min) | $1.15 \times 10^3$ |
| 140 min. (4 hr) | $2.86 \times 10^3$ |
| 170 min. (4 hr 30 min) | $2.75 \times 10^2$ |
| 100 min. (5 hr) | 10–100 |
| 160 min. (6 hr) | 0 |
| 0.89 log reduction in 2 hours | 7.1205739 |
| | 6.2304489 |
| | 0.8901250 |
| 7.12 log reduction in 6 hours. | 7.1205739 |
| Approximate D value = 50.56 minutes | 0.0000000 |
| (1 log reduction per hour) | 7.1205739 |

It should be noted that the spores used in this test are the most resistant type to sporicides.

Summary of Sporicidal Studies

D value (Log Reduction/Time) is the time required for a ten-fold reduction of viability

| Concentration of Composition A tested | D-Value |
| --- | --- |
| 5.0% | 48 minutes |
| 7.5% | 50 minutes |
| 15% | 15.2 minutes |

EXAMPLE 3

To determine the effect of temperature on the sporicidal activity of Composition A (from Example 1), Clostridium sporogenes organisms ($10^6$ resistant to HCl) were dried on pennicylinders and treated with various concentrations at 20° C. and 50° C. The results are shown in the on following table:

| | Sporicidal Activity | | |
| --- | --- | --- | --- |
| COMPOSITION A Concentration | Temp. C. | Time Minutes | Clostridium sporogenes Pennicylinders #Sterile/#Tested |
| 1.0% | 20 | 15 | 00/20 |
| 0.2% | 50 | 15 | 10/10 |
| 1.0% | 50 | 15 | 19/20 |

It can be seen that upon raising the temperature from 20° C. to 50° C., a significant increase in sporicidal activity was achieved.

EXAMPLE 4

An additional demonstration of the effectiveness of the present methods is in using Composition A (from Example 1) to kill fungal spores. Fungal spores are discharged from species such as thermally stable fungi that infect fruit and vegetables and thereby cause severe spoilage. The following data show the effectiveness of the present composition as a sporicide against fungal spores:

The peroxide-based compositions of the present invention were tested for activity against fungal spores.

A determination was made as to what concentration did Composition A commence to exhibit a kill effect on the fungal spores. Thus, fungal spores were exposed to both 0.1% and 0.25% concentrations of Composition A and recovery was made at several intervals up to 20 minutes. The 0.1% concentration commenced to exhibit a kill effect after about 10 minutes exposure. Approximately a 30% decrease in survivors was detected after 20 minutes exposure. At the 0.25% concentration, a kill effect was observed after 1 minute exposure. There was approximately a 70% decrease in viability after 20 minutes exposure. The results are summarized below:

| Exposure of Fungal Spores to Composition A | |
| --- | --- |
| Exposure Time (minutes) | Survivors 1% Composition A |
| 1 | 0 |
| 30 | 0 |
| 60 | 0 |

Initial Count = $1.4 \times 10^5$/ml

EXAMPLE 5

Composition A (from Example 1) was subjected to a use—dilution test per the method in the 14th Edition, A.O.A.C., Section 4.005 through 4.011. The conditions were at 200 ppm hardness as determined per the 14th Edition A.O.A.C., Section 4.025.

The test organisms were:
1. *Pseudomonas aeruginosa*, ATCC #15442.
2. *Staphylococcus aureus*, ATCC #6538.
3. *Salmonella cholerasuis*, ATCC #10708.

All test organisms were analyzed for their reaction to the time/concentration requirements outlined in the above-mentioned A.O.A.C. All three organisms gave satisfactory responses to phenol (phenol coefficient).

The following results were obtained:

| TEST ORGANISM | NO. OF CARRIERS | NO. (+) FOR GROWTH |
|---|---|---|
| *P. aeruginosa*, ATCC #15422 | 60 | 0/60 |
| *S. aureus*, ATCC #6538 | 60 | 0/60 |
| *S. cholerasuis*, ATCC #10708 | 60 | 0/60 |

All tubes were subcultured for 48-hours in both Fluid Thioglycolate and Letheen broth. All results were negative.

EXAMPLE 6

In order to demonstrate the effectiveness of the composition of this invention, Composition A (from Example 1) was prepared at 0.5% and 1% W/V in sterile water and tested against pure isolates of the organisms listed below:

| ORGANISMS ($10^6$/ml) | SOURCE OF ORGANISMS | SURVIVING ORGANISMS |
|---|---|---|
| *Escherichia coli* | Breeder Farm | 0 |
| *Staphylococcus aureus* | Broiler Farm | 0 |
| *Salmonella species* (paratyphoid) | Farm #1 | 0 |
| *Klebsiella pneumoniae* | Hatchery #2 | 0 |
| *Citrobacter freundii* | Hatchery #2 | 0 |
| *Proteus mirabilis* | Hatchery #2 | 0 |
| *Pseudomonas aeruginosa* | Hatchery #3 | 0 |
| *Streptococcus cereus* | ATCC | 0 |
| *Aspergillis fumigatas* | Hatchery #2 | 0 |
| *Listeria monocytogenes* | Hatchery #2 | 0 |

Twelve sets of a two-fold dilution series was made for each of the disinfectants in sterile deionized water. To each tube in a given set, twenty microliters of a given broth culture were added. Tubes were incubated at room temperature for one hour. After the incubation period, one milliliter of each dilution was plated on non-selective media and incubated for 48 hours at 37° C. After the 48 hours of incubation, results were recorded. No surviving organisms were detected.

EXAMPLE 7

Composition A (from Example 1) of this invention was tested to demonstrate the elimination of Listeria monocytogenes from aqueous mixtures of sheep blood.

The pour plate procedure was used to determine the presence of Listeria monocytogenes after exposure to varying concentrations of the compositions supplemented with 5% sheep blood. Tests were run in duplicate with plates poured in triplicate. Plates were incubated at 30° C. for 48 hours. No attempt to adjust the pH was made. The compositions were prepared in sterile deionized water. The pH values of Composition A ranged from 10.4 to 10.5.

The results are shown in the following table:

| | | DILUTION | | |
|---|---|---|---|---|
| | | 0.05% | 0.1% | 1.0% |
| 1 minute: | Sample A | TNTC* | N.D. | N.D. |
| 5 minutes: | Sample A | E50,000** | N.D. | N.D. |
| 10 minutes: | Sample A | N.D. | N.D. | N.D. |

*TNTC = Too numerous to count.
** = Estimate
ND. = None detected, triplicate, 1 Ml. Plating
INITIAL LEVELS OF INNOCOLUM
Sample A = $6 \times 10^6$ per ml.

The product is effective in eliminating Listeria monocytogenes under the conditions tested. Listeria monocytogenes will tolerate alkaline pH's better than most organisms. This shows that the conditions generated by this product are more effective against other organisms normally involved in disinfectant testing.

EXAMPLE 8

A study was performed on the compositions of the invention with respect to the anti-microbial properties as related to the compositional ratio of the components, namely, sodium carbonate-hydrogen peroxide, quaternary ammonium salt (N-(n-alkyl-benzyl-dimethyl) ammonium chloride and nonionic detergent (polyethoxy and polypropoxy block polymer). *Pseudomonas aeruginosa* as used at a mean bacterial level $1.28 \times 10^7$ organisms/ml with a contact time of 5 minutes. The results are given below:

| EXPERIMENTAL RESULTS *PSEUDOMONAS AERUGINOSA* | | | | | | | | |
|---|---|---|---|---|---|---|---|---|
| PERCENTAGE % | | | LOG REDUCTION FACTOR (LRF) SOLUTION CONCENTRATION g$l^{-1}$ | | | | | |
| *PCS | *QUAT | *PLUR | 20 | 15 | 10 | 5 | 2.5 | 1.0 |
| 100 | 0 | 0 | +++ | +++ | 4.3 | --- | --- | --- |
| 80 | 10 | 10 | +++ | +++ | +++ | +++ | +++ | 5.1 |
| 80 | 20 | 0 | +++ | +++ | +++ | +++ | +++ | +++ |
| 80 | 0 | 20 | +++ | 4.3 | 5.0 | --- | --- | --- |
| 70 | 10 | 20 | | | | | | +++ |
| 70 | 20 | 10 | | | | | | +++ |
| 60 | 40 | 0 | +++ | +++ | +++ | +++ | +++ | +++ |
| 60 | 10 | 30 | | | | | | +++ |
| 60 | 20 | 20 | +++ | +++ | +++ | +++ | +++ | +++ |
| 60 | 30 | 10 | | | | | | +++ |
| 60 | 0 | 40 | +++ | +++ | +++ | +++ | --- | --- |
| 50 | 0 | 50 | | | | | 4.1 | --- |

-continued

**EXPERIMENTAL RESULTS *PSEUDOMONAS AERUGINOSA***

| PERCENTAGE % | | | LOG REDUCTION FACTOR (LRF) SOLUTION CONCENTRATION $gl^{-1}$ | | | | | |
|---|---|---|---|---|---|---|---|---|
| *PCS | *QUAT | *PLUR | 20 | 15 | 10 | 5 | 2.5 | 1.0 |
| 50 | 10 | 40 | +++ | +++ | +++ | +++ | +++ | +++ |

LRF < 3 = ---
LRF > 6 = +++
PCS = Sodium percarbonate
QUAT = Tetradecyl-dimethyl-benzyl-ammonium chloride
PLUR = Polyethoxy and Polypropoxy block polymer

EXAMPLE 9

In food processing plants, the principal sites of microbial contamination are the floors, drains, conveyor belts, complex process equipment, cutting boards and steel mesh gloves. Additional areas include walls, ceilings, counters, refrigeration units, boot dips, hand dips, truck interiors, and fryers.

As an example of the utility of the composition in a food processing plant, studies were carried out in a poultry plant on heavily contaminated steel mesh gloves as follows:

Three sets of 12 pairs of steel mesh gloves, heavily enmeshed and contaminated with meat and fat particles were hosed with high pressure water (160° F.). One set was placed in polyethylene bags and extracted with a bacterial media and cultured (incubated) in broth media at room temperature for one hour. One milliliter was plated on non-selective media and incubated for 48 hours at 98° F.

Similarly, the remaining sets were treated as follows:

a) One set was placed in a 5% W/V solution of Composition A (from Example 1). Exposure time was 5 minutes.

b) One set was placed in a 5% W/V solution of Composition A (from Example 1) within an ultra-sonic generator (Branson Co.) and sonicated for 1 minute.

The untreated steel mesh gloves showed organisms such as *Escherichia coli* and *Salmonella enteridites* on the plates having 3 billion to "too numerous to count." The steel mesh gloves after treatment with 5% solution and 5% solution with sonication had zero counts.

EXAMPLE 10

Polyurethane surgical scrub brushes (2 in. × 3 in. × 1 in.) were prepared by forming interior pockets and inserting varying amounts of the powdered mixture of Composition A (from Example 1). After the powdered mixture of Composition A was added, the incisions in the sponges were sealed with plastic adhesive. Both sides of each sponge were then impregnated with 1 ml. of a 20% by weight solution of polyethoxy and polypropoxy block polymer in isopropanol. The isopropanol solvent was then allowed to evaporate.

A Pseudomonas aeruginosa culture of $10^6$ per ml organisms on a glass surface was rendered disinfected after 5 minute exposure, as shown by bacteria swab culture.

EXAMPLE 11

A further demonstration of the fungicidal activity of Composition A (from Example 1) of the invention was shown by employing *Candida albicans* (yeast) obtained from the National Type Collection of Yeast Cultures (Norwich, U. K.). The yeast spores were at a level of at $10^6$ yeasts/ml in the initial solution which contains 8.0 g/l plasma. At a contact time of five minutes, 1.56% of Composition A effected a complete kill, i.e, a log reduction greater than 6.

EXAMPLE 12

A test was performed to evaluate the hard surface detergency of composition A (from Example 1). Vinyl tiles were soiled with modified urban soil consisting of clays, oils, fatty acids, iron oxide, and hyperhumus. The soiling was accomplished by applying with a brass roller to the tiles. A Gardener Tester (automatic washer) (Gardener Co., Rockville, Md.) was used with 50 ml of a 1% W/V concentration of Composition A. To measure the detergency effectiveness, reflectance measurements were obtained. The test results indicated that 41% of the soil was removed. This result is comparable to the effectiveness of commercially available products such as BTC2125 MP-40 (Stepan Co.).

EXAMPLE 13

Biofilms were prepared according to the method of Dr. Zatola of the University of Minnesota (1989) on stainless steel cylinders. The cylinders were charged with Listeria monocytogenes and Salmonella enteritides at $10^6$ levels. Five of the cylinders were respectively dipped in (1) bleach (300 ppm), (2) bleach (500 ppm) (3) iodine (200 ppm), (4) quat (4000 ppm) and (5) 3% W/V of Composition A (from Example 1). The exposure time was 5 minutes. All chemically treated cylinders were monitored by means of a Bacterometer. With the exception of Composition A, all showed growth within 24 hours whereas the cylinder treated with Composition A showed no growth even after 48 hours at incubation temperature of 37.5° C.

While only a few exemplary embodiments of this invention have been described in detail, those skilled in the art will recognize that there are many possible variations and modifications which may be made in the exemplary embodiments while yet retaining many of the novel and advantageous features of this invention. Accordingly, it is intended that the following claims cover all such modifications and variations.

We claim:

1. A method of sterilizing objects or surfaces which comprise applying to objects or surfaces contaminated with ascospores a sterilizing effective amount of a composition in aqueous solution in a 0.1–1.0% concentration (W/V), said composition consisting of 70% (wt) of an alkaline water-soluble salt having hydrogen peroxide of crystallization with sodium carbonate, 20% (wt) of tetradecyldimethyl-benzyl-ammonium chloride and 10% (wt) of ethoxypropoxy block polymer.

2. The method of claim 1 wherein and the effective amount of said composition is a 1.0% concentration applied for 15 to 25 minutes at about 20° C.

3. The method of claim 1 wherein said composition is applied as a liquid bath.

4. A method of sterilizing objects or surfaces which comprises applying to objects or surfaces contaminated with bacterial spores at a $10^6$/ml to $10^7$/ml level a sterilizing effective amount of a composition comprising from about 10% to about 90% by weight of an alkaline water-soluble salt having hydrogen peroxide of crystallization and from about a fraction of a percent to about 30% by weight of a positively charged phase-transfer agent selected from the group consisting of a phosphonium salt, a sulfonium salt, and a quaternary ammonium salt, said composition in aqueous solution forming both a water and lipid soluble phase-transfer ion-pair and said composition being applied for exposure times up to 4 hours at ambient temperature, to result in 100% kill.

5. The method of claim 4 wherein said bacterial spores are selected from the group consisting of *Clostridium sporogenes* and *Bacillus subtilis*.

6. The method of claim 4 wherein said composition is present at a concentration of 5.0% to 15% (W/V).

7. The method of destroying and removing biofilms from objects or surfaces which comprises applying to said objects and surfaces contaminated with biofilms, a destroying and removing effective amount of a composition comprising from about 10% to about 90% by weight of an alkaline water-soluble salt having hydrogen peroxide of crystallization and from about a fraction of a percent to about 30% by weight of a positively charged phase-transfer agent selected from the group consisting of a phosphonium salt, a sulfonium salt, and a quaternary ammonium salt, said composition in aqueous solution forming both a water and lipid soluble phase-transfer ion-pair and said composition being applied to said objects or surfaces at a concentration of 0.1% to 20% (W/V) for exposure times of 1 minute to 4 hours at ambient temperatures.

8. A method of treating objects or surfaces wherein said treatment consists of combined cleaning, sanitizing, disinfecting, sterilizing and effecting sporicidal and fungicidal activity, which method comprises applying to objects or surfaces in need of cleaning, sanitizing, disinfecting, sterilizing, sporicidal activity and fungicidal activity, an effective amount of a composition comprising from about 10% to about 90% by weight of an alkaline water-soluble salt having hydrogen peroxide of crystallization and from about a fraction of a percent to about 30% by weight of a positively charged phase-transfer agent selected from the group consisting of a phosphonium salt, a sulfonium salt, and a quaternary ammonium salt, said composition in aqueous solution forming both a water and lipid soluble phase-transfer ion-pair.

* * * * *

UNITED STATES PATENT AND TRADEMARK OFFICE
CERTIFICATE OF CORRECTION

PATENT NO. : 5,320,805
DATED : June 14, 1994
INVENTOR(S) : Kramer et al.

It is certified that error appears in the above-indentified patent and that said Letters Patent is hereby corrected as shown below:

Column 2, line 12, change "sporioidal" to --sporicidal--; and

Column 4, line 17, change "t-butyl phosphonium iodide" to
   --tetra-n-butyl phosphonium iodide--.

Signed and Sealed this

Eighteenth Day of October, 1994

Attest:

BRUCE LEHMAN

Attesting Officer

Commissioner of Patents and Trademarks